United States Patent
Steiner et al.

(10) Patent No.: US 8,624,190 B2
(45) Date of Patent: Jan. 7, 2014

(54) METHOD AND DEVICE FOR DETERMINING THE SEX OF FERTILIZED, NON-INCUBATED BIRD EGGS

(75) Inventors: Gerald Steiner, Schwarzenberg (DE); Edmund Koch, Dresden (DE); Maria-Elisabeth Krautwald-Junghanns, Markleeberg (DE); Thomas Bartels, Gehrden (DE)

(73) Assignees: Technische Universität Dresden, Dresden (DE); Universität Leipzig, Leipzig (DE)

( * ) Notice: Subject to any disclaimer, the term of this patent is extended or adjusted under 35 U.S.C. 154(b) by 0 days.

(21) Appl. No.: 13/574,751

(22) PCT Filed: Jan. 14, 2011

(86) PCT No.: PCT/DE2011/000062
§ 371 (c)(1),
(2), (4) Date: Jul. 23, 2012

(87) PCT Pub. No.: WO2011/088825
PCT Pub. Date: Jul. 28, 2011

(65) Prior Publication Data
US 2012/0318981 A1  Dec. 20, 2012

(30) Foreign Application Priority Data
Jan. 21, 2010 (DE) .................. 10 2010 006 161

(51) Int. Cl.
*G01J 5/02* (2006.01)
(52) U.S. Cl.
USPC ...................... 250/339.08; 119/6.8

(58) Field of Classification Search
USPC ............. 250/339.01–339.09, 339.11–339.15; 119/6.8
See application file for complete search history.

(56) References Cited

U.S. PATENT DOCUMENTS

| 4,835,389 A | 5/1989 | Doyle |
| 5,170,056 A | 12/1992 | Berard et al. |

(Continued)

FOREIGN PATENT DOCUMENTS

| DE | 100 30 927 | 5/2002 |
| DE | 10200703 107 | 9/2008 |
| EP | 1118 267 | 7/2001 |

OTHER PUBLICATIONS

"Sexing of Turkey Poults by Fourier Transform Infrared Spectroscopy" by Gerald Steiner, Thomas Bartels, Maria-Elisabeth Krautwald-Junghanns, Alois Boos, Edmund Koch, Anal Bioanal Chem, Published online on Nov. 20, 2009—Germany.

*Primary Examiner* — David Porta
*Assistant Examiner* — Taeho Jo
(74) *Attorney, Agent, or Firm* — Horst M. Kasper (57) ABSTRACT

The invention relates to a method and a device (1, 100) for determining the sex of fertilized, nonincubated bird eggs (13, 130), where an egg (13, 130) has a solid egg shell (14), an egg yolk (2) which is surrounded by the egg shell and further egg integuments and a blastodisc (3) associated with the egg yolk (2), and where a probe (4, 40) for measuring a spectrum is introduced through a hole (17) of the egg shell (14) towards the blastodisc (3) with blastodisc cells (23), with the following steps: —positioning of the probe (4, 40) in the region of the blastodisc (3), —spectroscopic in-ovo characterization of the blastodisc cells (23), and —identification of the sex by an automatic classification of spectra.

23 Claims, 7 Drawing Sheets

(56) References Cited

U.S. PATENT DOCUMENTS

| | | | |
|---|---|---|---|
| 5,459,316 A * | 10/1995 | Doyle | 250/339.11 |
| 5,703,366 A | 12/1997 | Sting et al. | |
| 6,029,080 A * | 2/2000 | Reynnells et al. | 600/407 |
| 6,244,214 B1 * | 6/2001 | Hebrank | 119/6.8 |
| 7,089,879 B2 * | 8/2006 | Wolfe | 119/6.8 |
| 7,167,579 B2 * | 1/2007 | Taniguchi | 382/110 |
| 7,249,569 B2 * | 7/2007 | Mendu et al. | 119/6.8 |
| 7,354,401 B1 * | 4/2008 | Toelken | 600/443 |
| 7,615,759 B2 * | 11/2009 | Kimura et al. | 250/458.1 |
| 7,650,013 B2 * | 1/2010 | Dietsch et al. | 382/103 |
| 7,950,349 B1 * | 5/2011 | Rollins | 119/6.8 |
| 8,364,247 B2 * | 1/2013 | Opitz et al. | 600/477 |
| 2003/0172392 A1 | 9/2003 | Mendu et al. | |
| 2007/0137577 A1 * | 6/2007 | Wolfe et al. | 119/6.8 |
| 2008/0289578 A1 * | 11/2008 | Rybarczyk et al. | 119/6.8 |
| 2011/0144473 A1 * | 6/2011 | Opitz et al. | 600/407 |
| 2012/0058052 A1 * | 3/2012 | Decuypere et al. | 424/9.6 |

* cited by examiner

METHOD AND DEVICE FOR DETERMINING THE SEX OF FERTILIZED, NON-INCUBATED BIRD EGGS

The invention relates to a method and apparatus for determining the sex of fertilized and not embryonated bird eggs, wherein an egg exhibits a solid egg shell, an egg yolk surrounded by one of the egg shells and further fetal membranes, a germinal disc having associated with the egg yolk and wherein a probe for measuring a spectrum is led through a hole in the egg shell guided toward the germinal disc with the germ disc cells,
comprising the steps of
- Positioning of the probe in the region of the embryonic disc,
- Spectroscopic characterization in-ovo of the embryonic disc cells,
- Identification of sex by an automatic classification of Spectra.

It is important here for example with birds and, also reaching into economic areas, especially with poultry the determination whether to develop as individuals for example from previously fertilized eggs either males or females.

There is already described a method for sex determination of chicks by means of infrared Fourier transform spectroscopy in the publication Steiner et al. Sexing of turkey poults by Fourier transform infrared spectroscopy, Analytical and Bio-analytical Chemistry, Vol 396 (1) 2010 pages 465-470 which allows to determine the sex of six-week-old chicks.

The use of infrared spectroscopy for the determination of the sex of young birds shows that the method is fast and precise, and can be potentially used by the poultry industry to identify and select eggs with female embryonic stage or male embryonic stage for breeding purposes.

A multitude of birds, especially nestlings and farmers, veterinarians, aviculturists and ornithologists, however, the exact sex embryonic stages of birds show no external sexual characteristics. For poultry-determination is a fundamental aspect. But for the poultry industry, the knowledge is of paramount importance: fast, objective and inexpensive procedures for possible early sex determination, for example, in chickens and turkeys, are for the poultry industry important because in the preferred gender for incubation can be identified.

The Fourier transform infrared spectroscopy is used for this purpose. The method is based on that cells extracted from the growing contour springs of six weeks old, male and female turkeys are employed. The technique exploits the cellular genetic information and allows a direct determination of the sex of the bird.

One problem comprises that the effort to determine the specific gender involves many steps and therefore the time expenditure is very high.

A method for determining the sex of birds is described in the German Patent Application publication DE 10 2007 013 107 A1, wherein DNA-relevant cellular material of the sexually to be determined bird was studied with light and the molecular oscillations are measured, wherein the light generated spectrum of molecular vibrations is recorded and compared with predetermined reference spectra of gender-specific DNA structures of the to be investigated bird species. A sex assignment of the bird is rendered based on the basis of the DNA content of the cell material.

The molecular oscillations are measured here by means of application of Raman spectroscopy, or IR spectroscopy, it being possible for example, the relevant DNA cellular material can be removed from the stem of a young spring of a bird. The cell material is prepared on a support and is scanned with light.

In another sub-method the light is focused for measuring the molecular vibrations of the DNA relevant cell material from unhatched birds through the egg shell and onto the embryo or germ-disc, wherein the spectrum of the radiation generated by molecular oscillations in the egg is measured with a probe guided through the shell of the egg.

At least a microscopically small hole is drilled through the eggshell for the passage of the probe for measuring the spectrum. The light through the small opening through the eggshell is immediately focused on the germinal disc as cell material. The probe is inserted by the same or other access of small opening size, by means of the reflected spectrum and is measured by the probe recorded spectrum of the afore mentioned molecular motion in the interior of the egg.

The resulting spectral information are compared with reference data in a second step and are fed to a classification algorithm. These represent preferably statistically derived data on the bird species to be examined. The assignment of gender of the DNA material to be investigated is made from this comparison One problem comprises that a high time expenditure is required for the insertion of a probe into pre-made holes for a very large number of bird eggs to be examined. In addition, with a focusing of the light from the probe to the germinal disc, a considerable adjustment has to be furnished for an optical imaging, wherein the focusing plane can exhibit a different position from egg to egg and no determination of the sex can be carried out therewith.

No arrangement is given how the IR spectrum of the germinal disc cells under in-ovo conditions can be taken quickly and reliably.

A spectroscopy device is described in the U.S. Pat. No. 4,835,389 A, which contains a total reflection element which is disposed at the bottom of a long probe tube that is together with the total reflection element deeply immersed in a container with liquid in order to capture with the complete surface of the crystal and immersed in the liquid and many edge side total reflections within the crystal and to receive analytical information on an optical path received and forward them to the spectroscopic device.

An immersion probe is described in U.S. Pat. No. 5,459,316 A, which probe is immersed in powder or liquid and an infrared spectroscopy is performed with it. The immersion probe consists of at least one tube, which tube exhibits a built-in attenuated total reflection ATR element operating on the basis of attenuated total reflection (ATR) at the bottom. The ATR element furnished serves as a back reflector.

A refractometric method for a long-term stable measurement of concentrations of dissolved substances and a device for performing the process are described in the publication German patent DE 100 30 927 C1, wherein a linearly polarized electromagnetic measuring radiation beam is guided by total reflection in a prism. Here the longitudinal sides and a narrow side of the prism are in contact with the solution to be measured. Inside the prism made Edge side multiple total reflections of the measuring radiation beam are fed to a detector after they emerge from the prism via phase shifter and analyzer to a detector, wherein the concentration is determined from the signals and from a calibration curve.

An ATR-probe for measurement of whole blood is described in the document U.S. Pat. No. 5,170,056 A, wherein measurement solutions can be measured remote from the spectrometer through a light conductor. Here, the ATR probe is a portion of a fiber optic coupled device for carrying out IR-spectroscopy. The long cylindrical ATR probe crossing the solution exhibits coupled connectors of the light guides at the two front sides, wherein the infrared radiation is passed through the ATR probe over the coupled connectors. The detected IR radiation is measured and used for parameter determination of the blood from the many attenuated edge side total reflections within the ATR probe during the passage of the radiation bundle through the ATR probe.

There are problems that can occur in that falsifications can occur in the detected spectra based on the configurations of the recited probes with the multitude of total reflections on the edge sides and that with the total reflection bundles detected no precise positioning of the crystal tip on blastoderm cells is possible. Thus, no precise determination of the sex of bird eggs can be performed.

It is therefore the object of the present invention to provide a method and an apparatus for determining the sex of fertilized and non-incubated bird's eggs, which are so designed to be suitable, that sex can be unequivocally determined quickly and reliably already in the eggs.

The object is solved by a method having the features of claim 1 and an apparatus having the features of claim 8.

The procedure for determining the sex of fertilized and non-incubated bird's eggs, wherein one egg comprises a solid egg shell, an egg yolk surrounded by the eggshell and other egg cases and an embryonic disc coordinated to the egg yolk, with a probe for the measurement of a spectrum through a hole in the egg shell through is guided toward the germinal disc with germ disc cells, includes the following steps
   Positioning of the probe in the region of the embryonic disc,
   Spectroscopic in-ovo characterization of the embryonic disc cells
   Identification of sex through automatic classification of reflective spectra
wherein according to the characterizing part of patent claim 1 an optical crystal is used as a probe, and wherein rapid and non-reactive receiving of an infrared spectrum and/or near infrared spectrum is performed with the optical crystal, with use of the attenuated total reflection within the optical crystal by the evanescent field in the region of the germinal disc, wherein the attenuation/extinction due to a spectral absorption of gender germinal disc cells takes place, wherein the positioning of the optical crystal is accompanied by a permanent automatic evaluation of the recirculated spectra up to a determination of gender specific germinal disc cells, until the spectrum is evaluated by an evaluation unit and the sex of the fertilized egg is unequivocally displayed by a display unit.

The advantages include that no material must be removed in the conduct of the processing of the egg. Also, there are no foreign substances introduced for signal detection in the egg. In addition, no entry is made of energy, such as heat or light.

The automatic positioning of the optical crystal with respect to the germinal disc cells with the crystal tip or output surface is carried out until the evanescent field of the total reflection at the crystal tip or output face captures the germinal disc and the crystal is finally brought into a final disc coordinating position, in which the evanescent field enters into interaction with the germ disc cells and thus an extinction becomes registrable.

The positioning of the optical disk mapping crystal can be oriented in all directions in space possible in order to hit the germinal disc with the germinal disc cells as precisely as possible.

Continuously recirculated IR- and/or NIR spectra are recorded and fed to an evaluation during the positioning operation, wherein an automatic classification of the spectra using the spectral fingerprint, of for example, proteins, lipids and nucleic acids takes place.

In the gender-absorption of the incident IR and/or NIR light, the germ disc cells are identified based on absorption bands of nucleic acids (DNA and RNA) and other biochemical compounds such that the sex of the tested egg is determined and displayed.

The measurement can be performed with a conventional infrared spectroscopy.

Simultaneously, a plurality of bird eggs can be measured, wherein several optical crystals are disposed preferably equally spaced (array like) from each other and a plurality of optical crystals are arranged and coupled in each case with a separate optical fiber, or wherein the reflected light without fibers directly radiates onto an IR- and/or NIR-sensitive detector. In the latter case can also mirror/mirror systems can be employed for beam steering.

The inventive method is a procedure that is sufficiently precise for the poultry industry for the selection of eggs with female embryonic or male embryonic stages for breeding, egg production or fattening, wherein the killing of millions of chicks of the unwanted sex can be avoided shortly after hatching.

The apparatus for determining the sex of fertilized and non-incubated bird's eggs, wherein the egg includes a solid egg shell, a yolk surrounded by the eggshell and other egg envelopes, and germinal disc germ coordinated to the egg yolk, wherein a probe for measuring a spectrum is led through a hole of the eggshell and is guided toward the germinal disc in which the germinal disc cells, according to the procedure above,
contains according to the characterizing part of patent claim 8
   At least one egg position support for locking at least one egg,
   at least a height adjustment device with at least one support arm,
   At least one optical crystal formed as a probe, which optical crystal is fixed to the holding arm,
   At least one control unit for the egg arresting, egg position support and for the height adjustment device,
   At least one spectral light source related to at least one wavelength range that emits an IR and/or NIR light beam,
   At least one detector for receiving the recirculated IR and/or NIR light beam,
   At least one optical element for beam guidance guided between the light source and the optical crystal and the recirculated beam guidance from the optical crystal towards the detector, and
   One evaluation unit connected to the detector and a display unit, wherein the height-adjusting of the height of the retaining arm and thus of the optical crystal with respect to the location of the germinal disc is adjustable and the optical crystal is positioned in the region of the germinal disc in a disc mapping position in which disc mapping position over the optical crystal, an evanescent field overlaps the germinal disc, wherein the evanescent field forms in case of total reflection at the output area oriented toward the embryonic disc oriented output area, and the circulating germinal disc cells interact to make the evanescent field of a gender-specific absorption of light from the incident beam path, wherein said light is totally reflected at the output surface over the recirculated beam path within the crystal and finally is guided to the detector over the optical element for registration from which detector the registered spectral signals for analysis and display of sex are transmitted.

The disk mapping position of the optical crystal within the egg and in the region of the germinal disc can be obtained by a hole placed into the egg shell, wherein the hole is either already present or is placed during the installation of the optical crystal into the egg shell by the optical crystal itself.

The optical crystal can be furnished with differently structured crystal end faces or crystal ends, e.g. with a planar, a round or oval output surface or may be also provided with a pointed tip crystal.

The needle-shaped optical crystal can be formed in the lower output area oriented toward the embryonic disc.

The apparatus for determining the sex of fertilized and not incub\eggs, can have coordinated a device for detecting the position of the germinal disc within the egg, which device can be either part of the apparatus or may be formed separately.

The device for detecting the position of the germinal disc in the egg can be formed in the egg above the support arm, wherein the support arm is height adjustable and pivotable. The disk mapping position of the optical crystal e.g. bird eggs largely can be adjustable above and preferably perpendicularly in the region facing the germinal disc.

The device for detecting the position of the germinal disc in the egg can have at least one power supply and a signal technical line connected to the control unit of the device.

The device for detecting the position of the germinal disc in the egg can further also be connected to the height adjustment device and the egg position support pad.

The device for determining the position of the germinal disc, the height adjustment device and the egg position support pad can be connected in the control unit by means of program-technical means for coordinating the position of the germinal disc and the disc mapping position of the optical crystal, whereby the precision target mapping position of the optical crystal in the region of the germinal disc can be fixed.

The respective optical element for guiding the beam or the returning beam guidance can be a flexible optical fiber for the IR- and/or NIR light beam.

The optical crystal can be formed cylindrical and can be supported in a metal sheath, wherein the metal sheath is in connection with the support arm.

A gold layer can be applied between the metal sheath and the surface of the optical crystal for improving the reflection and/or the total reflection.

The optical crystal can be directed to the germinal disc in its disk allocation position with its lower output surface, wherein the germinal disc is at least in a part in the evanescent field for the absorption of IR- and/or NIR light.

The optical crystal can be constructed such that it leads the IR and/or NIR light beam and that a total reflection occurs at the tip in the region of the output surface.

The optical crystal can be made of IR-transparent and simultaneously hard material such as germanium, silicon, calcium fluoride ($CaF_2$), barium fluoride ($BaF_2$), zinc selenide (ZnSe) or zinc sulfide (ZnS).

The optical crystal can comprise glass or sapphire for measurements with NIR light.

The optical crystal can also consist of a composite, wherein the optical crystal in view of the needle shape the tip can be laid out as a diamond in the region of the output area.

The optical crystal can be connected to the flexible optical fiber, wherein the light beam is fed through fiber both from the spectral light source for IR and/or NIR light to the optical crystal and from the optical crystal to the detector.

Conventional spectrometers with broadband thermal sources, laser diodes or light sources with filters, in particular interference filters, can be used as spectral light sources for IR and/or NIR light.

A detector with many detector elements/pixels (focal plane array detector) can be used as IR- and/or NIR-sensitive detector to simultaneously and in parallel detect spectra of many bird eggs to be tested.

The advantage of the inventive apparatus is the possibility of a parallel measurement of many birds' eggs, and is thus a rapid simultaneous determination of the specific gender of bird eggs.

Further developments and further embodiments of the method and device are specified in further dependent claims.

The invention is further illustrated by way of several embodiments with reference to several drawings.

There is shown in.

Figure 1:
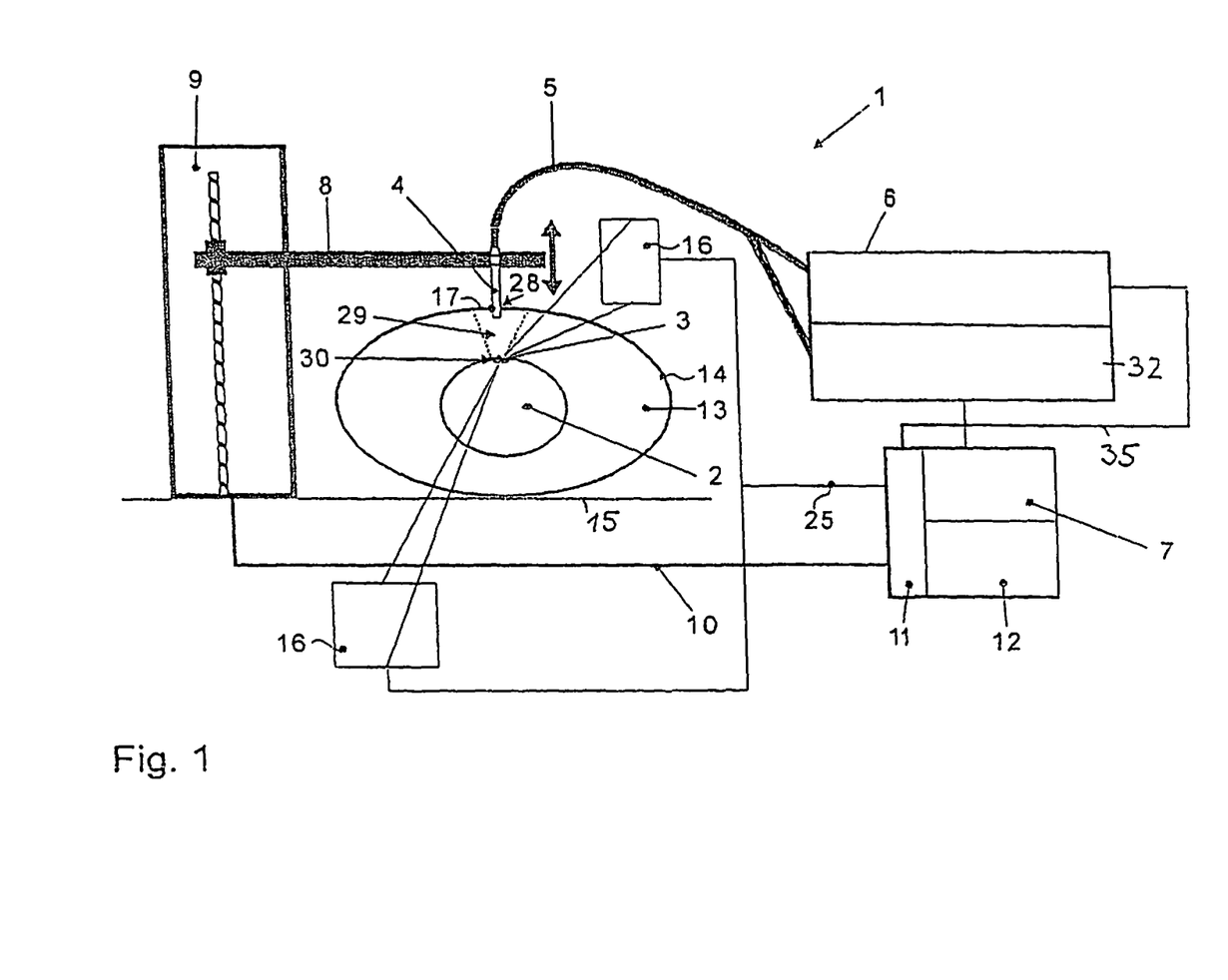
FIG. 1 shows a schematic representation of the apparatus for determining the sex of fertilized and not embryonated bird eggs, FIG. 2 an enlarged representation of the optical crystal during a spectrometric measurement of germinal disc cells of an avian egg in a disk mapping position.
Figure 2:
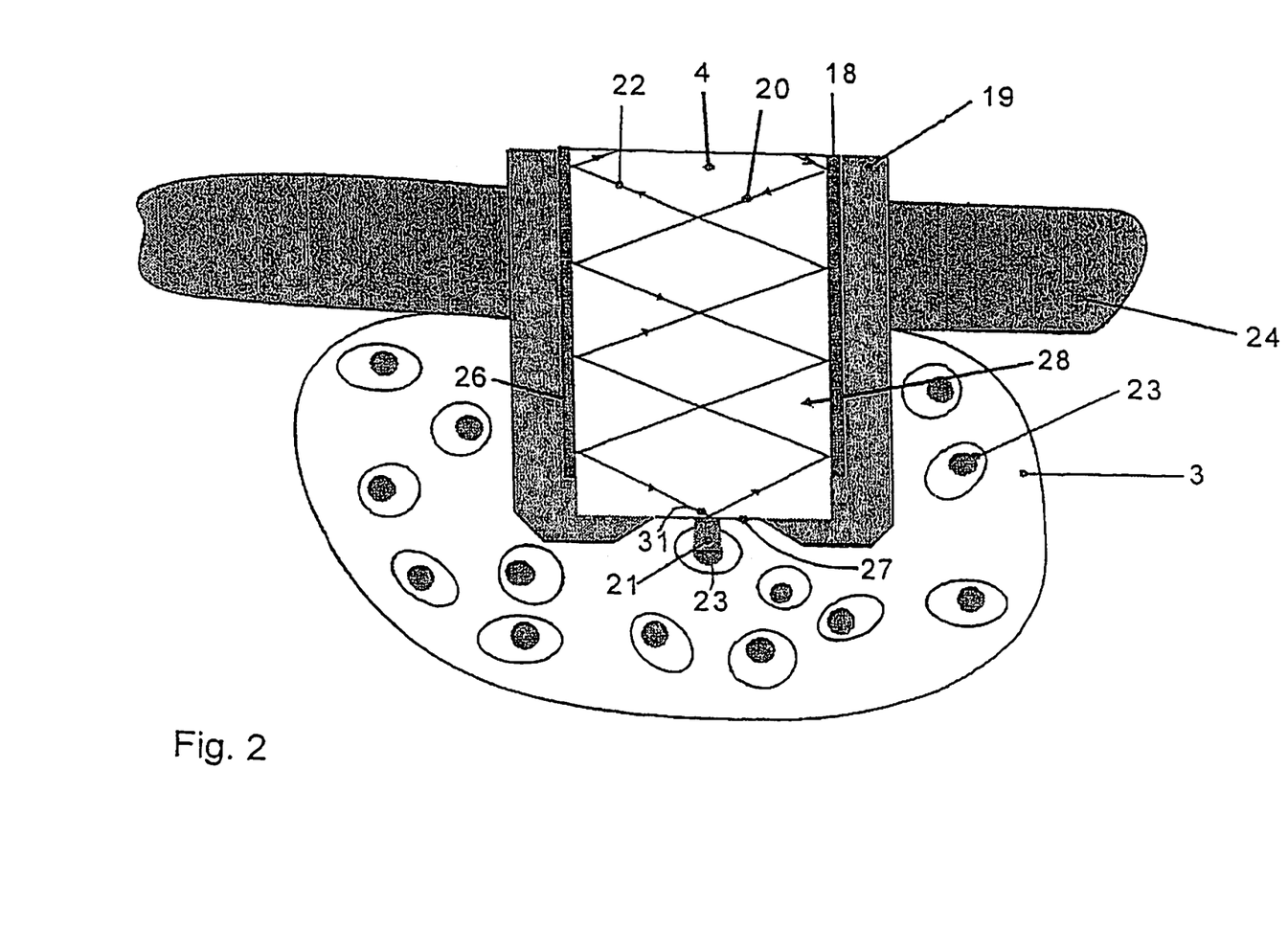

In the following, the two figures FIG. 1 and FIG. 2 are considered together.

In FIG. 1 is shown in a schematic representation of a device 1 for determining the sex of a fertilized and not incubated avian egg 13, wherein the avian egg 13 is an egg shell 14, an egg yolk 2, surrounded by the egg shell 14 and further fetal membranes and a germinal disc 3 coordinated to the egg yolk 2, and wherein a probe 4 for measuring a spectrum through a microscopically small hole 17 of the egg shell 14 is guided there through toward the germinal disc 3 with germinal disc cells 23, wherein the apparatus 1 comprises the following components/assemblies:

An egg positions support 15 with a locking of the avian egg 13,
- a height level adjusting device 9 with a supporting arm 8,
- an optical crystal formed as a probe, which probe is fixed to the support arm 8,
- at least one optical element 5 for a led beam guidance and recirculated beam guidance, a spectral light source 6 for IR and/or NIR light, wherein the spectral light source 6 stands in connection with the optical crystal 4 and emits light of a predetermined infrared and/or near infrared wavelength region, a detector 32 which receives the recirculated light through the optical element 5, At least one control unit 11 at least for the egg arresting egg-position-support 15 and for the height adjustment device 9, and the detector 32 connected to the evaluation unit 7 and a display unit 12, the height adjustment device 9, wherein the height of the support arm 8 and thus of the optical crystal 4 with respect to the location is adjustable with the height adjustment device 9 which is arranged above the egg yolk 2 germinal disc 3 and the optical crystal 4 in the area 29 positioned above the germinal disc 3 in a disk mapping position 28 is positionable, wherein an evanescent field 21, shown in FIG. 2 and forming upon total reflection 31, forms at the lower output area directed toward the germinal disk 3 and the circulating germinal disc cells 23, interact with the evanescent field 21 across the crystal 4 is shown, in the case of total reflection 31 at the lower, germ disc 3 related output surface 27 forming evanescent field 21 on the germinal disc 3 overlaps and the circulating germinal disc cells 23 interacting with the evanescent field 21 perform a gender-specific absorption of the light from the incident beam path 20, wherein the light totally reflected at the lower output surface 27 over the recirculated beam guide 22 within the optical crystal 4 and finally the optical element 5 is guided to the detector 32 so that through the optical crystal 4 different attenuated totally reflected light is submitted to the detector 32 for classifying and evaluating the gender indicator absorption.

A spectrometer can be used as a spectral light source 6 for IR and/or NIR light in FIG. 1.

The disc mapping position 28 of the optical crystal 4 provided in the region 29 above the germinal disc 3 by the hole 17 introduced in the egg shell 14 is shown in FIG. 1, wherein the hole 17 in the egg shell 14 either prior to introduction of the optical crystal 4 on the disk mapping position 28 is already present or during the passage of the optical crystal 4 through the eggshell 14 is made by the optical crystal 4 itself.

A device 16 for detecting the position 30 of the germinal disc 3 in the avian egg 13 can be preferably coordinated to the inventive device 1 in FIG. 1.

The device 16 for detecting the position 30 of the germinal disc 3 in the avian egg 13 can through the support arm 8, which can be constructed height-adjustable and pivotable, the position, in particular the disc mapping position 28 of the optical crystal 4 in the avian egg 13 can be installed largely above in a region 29 and preferably be set perpendicular to the germinal disc 3.

The support arm 8 can also be controlled through a control line 10 led to a height adjustment device 9 for installing a hole in the egg shell 14 with jerky or abrupt executable mechanical impulses, possibly accompanied by a short rotary turn.

The device 16 for detecting the position 30 of the embryonic disc 3 in the bird egg 13 may have at least one power supply and signal technology line 25 be connected to the control unit 11, which control unit 11 is technically connected through the line 35 to the spectral light source 6 for IR and/or NIR light energy supply and signal-line.

Here, the device 16 for detecting the position 30 of the germinal disc 3 in the avian egg 13 can be connected to the height adjustment device 9 and the egg position support 15 through the control line 10.

The device 16 for detecting the position 30 of the embryonic disc 3, the height adjustment device 9 and the egg position pad 15 can be connected by way of program-technical means to a joint coordination in the control unit 11, with the precision target mapping position 28 of the optical crystal 4 above the germinal disc 3 of the avian egg 13.

The practical process of measuring bird eggs at 13 is that the egg yolks 2 through the existing chalazae (chalaze cords) can rotate so that the germinal disc 3 is located in the upper part of egg yolk 2.

It is appropriate to determine the position 30 of the germinal disk 3 before the determination of gender by means of the device 16 for detecting the position 30 of the germinal disc 3. Only then can a hole installation and a disc mapping position 28 of the optical crystal 4 with respect to the germinal disc 3 can be performed by the controllable height adjustment device 9.

FIG. 2 shows an enlarged representation of the optical crystal 4 during the spectrometric measurement of absorption spectra of the embryonic disc cells 23 on the germinal disc 3 of an avian egg 13 is shown, wherein the optical crystal 4 is cylindrical and is supported in a metal sheath 19. The metal sheath 19 is, as shown in FIG. 1, in connection with the support arm 8. A thin gold layer 18 can be attached to the surface 26 of the crystal 4 between the metal sheath 19 and the surface 26 of the optical crystal 4 for improving the reflection or total reflection 31.

The jacket framed optical crystal 4 in its disc mapping position 28 is directed in FIG. 2 in his disk allocation position 28 with its lower jacket-free output area 27 directed toward the germination disc 3. Preferably, the disk mapping position 28 of the optical crystal 4 can be set through the yolk membrane 24 to pass directly over the germinal disc 3 for field overlapping on the evanescent field 21 in the embryonic disc cells 23.

The IR and/or NIR light guided out of the spectrometer 6 to the lower output area 27 of the crystal 4 oppositely positioned to the germinal disc 3 through the incoming guided beam 20 within the frame of beam guidance, wherein there through the beam set total reflection 31 the evanescent field 21 is formed and which evanescent field 21 depending on the absorption of IR and/or NIR light at the blastoderm cells 23 by absorption spectrally changes at the output area 27 crystalline side total-reflection optical beam path, 22 wherein the attenuated IR and/or NIR light of beam path 22 passes through the optical crystal 4 passes via the optical element 5 for guiding the beam to the detector 32 and following to the evaluation unit 7 for the spectral analysis.

Figure 3:
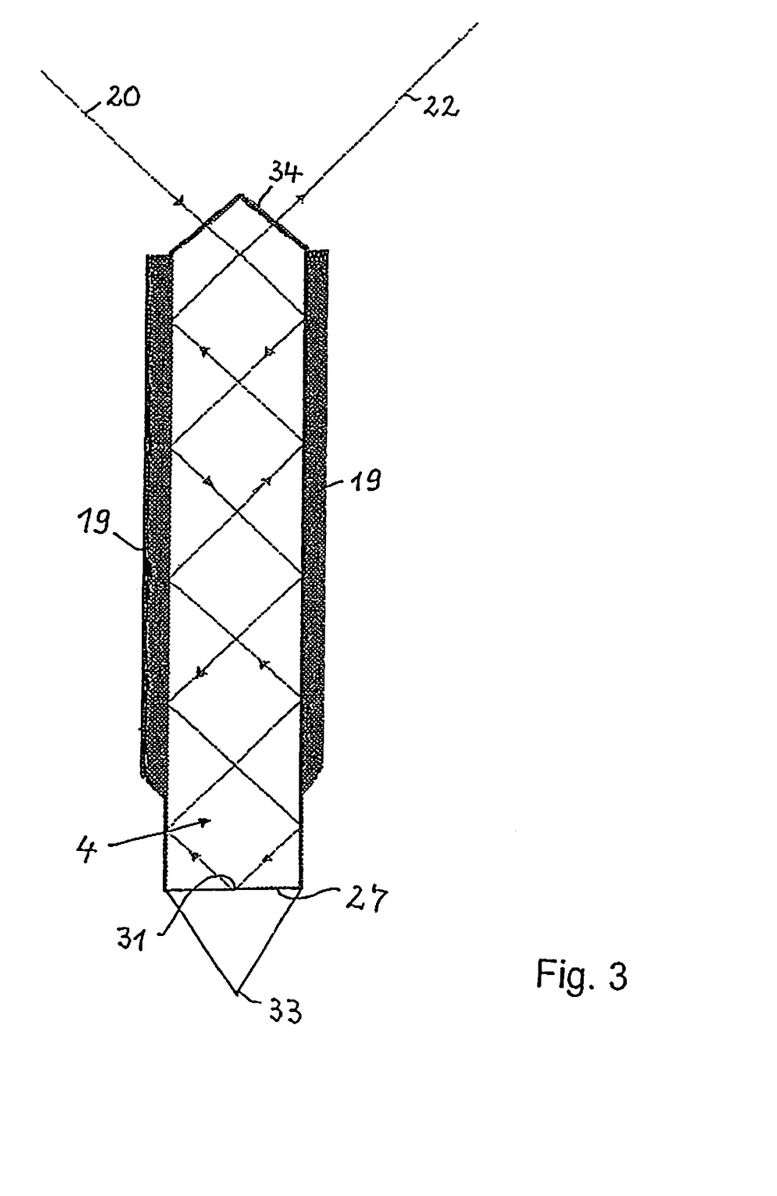
FIG. 3 shows an enlarged representation of the optical crystal with a tip to pierce the egg shell and forming a hole and with total reflection and outer surface, FIG. 4*a* infrared Fourier transform (FTIR) spectra of blastoderm cells of male bird eggs and of female bird eggs, wherein the arrows represent spectral regions for gender specific characterization/distinction.

FIG. 3 shows the optical crystal 4 is formed as a cylindrical body which has a crystal tip 33 in addition to its lower, germinal disc 3 related output area 27. The crystal tip 33 in FIG. 3 is cone shaped formed and serves also for the entry of the hole 17 through the egg shell 14. The optical crystal 4 has a cone face 34 disposed opposite to the output area 27 or to the cone tip 33, wherein the guided beam path 20 and the fed back beam path 22 are led through the cone face 34.

The crystal tip 33 of the optical crystal 4 can for example also formed needle shaped.

An essential point during the execution of the method is the cleaning/sterilization of the crystal tip and/or of the output area 27. For authentic recordings of the spectra neither foreign substances nor organisms/germs can be entered in the following bird eggs 13. Therefore, the inventive device 1 can be used to determine the gender of a fertilized not incubated avian egg 13 and a device for cleaning and sterilization (not shown) can be coordinated, which device for cleaning and sterilization after each measurement cleans and sterilizes the crystal tip 33. The device for cleaning and sterilization can perform on the basis of a steam sterilization and/or by chemical means. It may also penetrate any liquids into the intermediate space between the optical crystal 4 and the metal shell 19 or the reflecting gold layer 18. The device for cleaning and sterilization can be supported at the height adjustment device 9, and can be supported in the way the supporting arm 8 is supported and can be activated depending on the termination of the measuring process for cleaning and sterilization of the optical crystal 4 or the crystal tip 33.

The needle-shaped or cone-shaped crystal tip 33 may also consist of a synthetic or natural diamond. Diamond material, for example, sp3 carbon does not absorb the infrared and/or NIR light, is extremely hard and very insensitive to contamination with lipids, proteins, etc. In addition, the diamond material can be cleaned quickly.

Figure 4A:
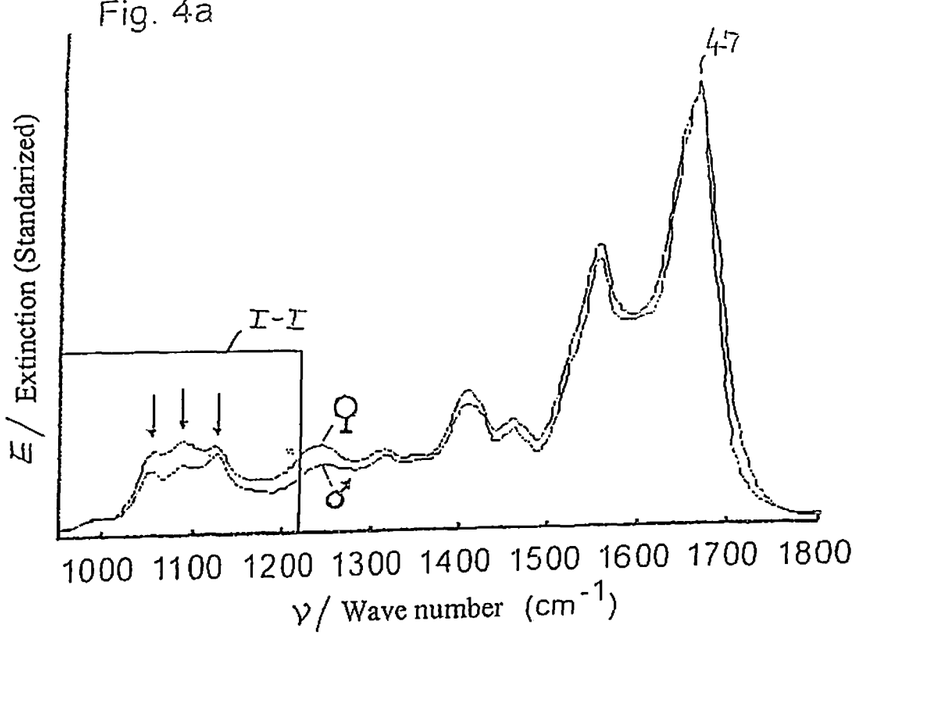
Figure 4B:
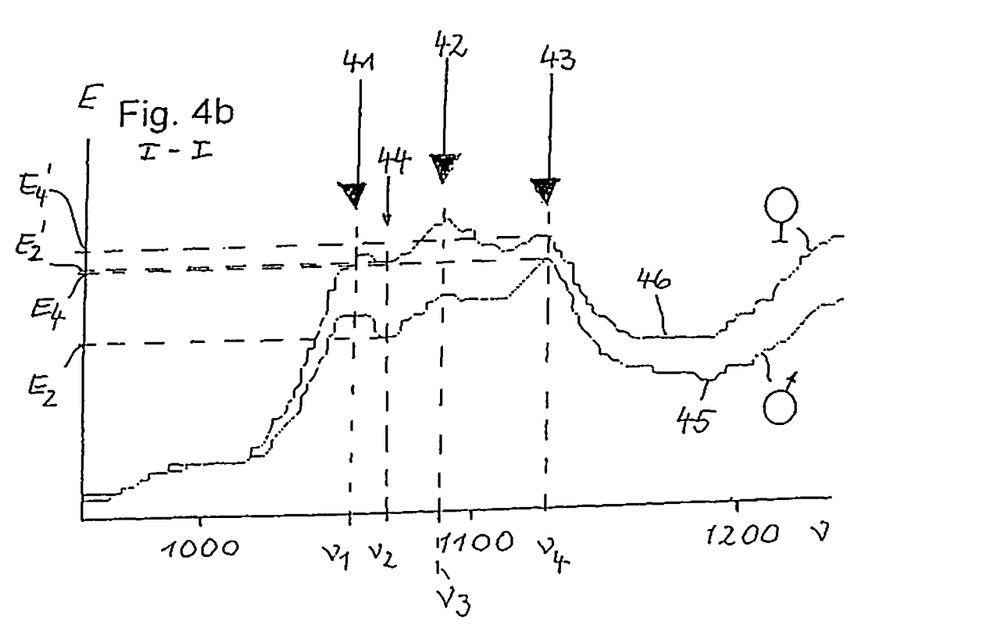
FIG. 4*b* shows an enlarged section of the evaluated (FTIR) spectra of FIG. 4*a* in the region of the arrows.

FIGS. 4a and 4b (higher magnification) are FTIR spectra 45, 46 of embryonic disc cells 23 male birds' eggs (45) and female bird eggs (46) is shown with the arrows 41, 42, 43, 44 representative for spectral ranges representing the gender characterization. The studies show that, for example three or four spectral regions 41, 42, 43, 44 for sex determination are sufficient, for example can be performed for a determination, a comparison of the absorbances in the absolute amounts: for the female sex is the absorbance between the wave numbers vi, v 2, v3, v 4 is greater than the extinction of the male running over the same wave numbers, so that a comparison in a wave number range can at least take place.

Another possibility is to determine the difference of the extinction E 4–E 2 (female)>E 4'–E 2' (male), as shown in FIG. 4b.

The sex determination is based here as the vibrations of the phosphate of DNA or RNA strands.

Therefore, an embodiment of the light source 6 with optical filters of the corresponding wave numbers vi, v 2, v 3, v 4 may be provided. It can be used instead of an expensive spectrometer 6 at least one or more laser diode/n or light source/n with a wave number associated filter, in particular an interference filter based on the wave numbers vi, v 2, V 3, v 4 be used, with the wave number v of the reciprocal of the wavelength λ (in microns) is multiplied-by 10000.

The method for determining the sex of fertilized and not embryonated bird eggs 13, wherein a bird's egg 13 is a solid egg shell 14, an egg yolk 2 surrounded by the egg shell and further fetal membranes and the egg yolk 2 coordinated to the germinal disc 3, wherein each for receiving one of the germinal disc 3 modified spectrum, a probe 4 is led through a microscopic hole 17 through the egg shell 14 in the direction towards the germinal disc 3,
has the following steps
  Positioning of the probe 4 in the region 29 of the embryonic disc 3,
  Spectroscopic in-ovo characterization of the embryonic disc cells 23,
  Identification of sex by an automatic classification of recycled spectra.

Figure 7:
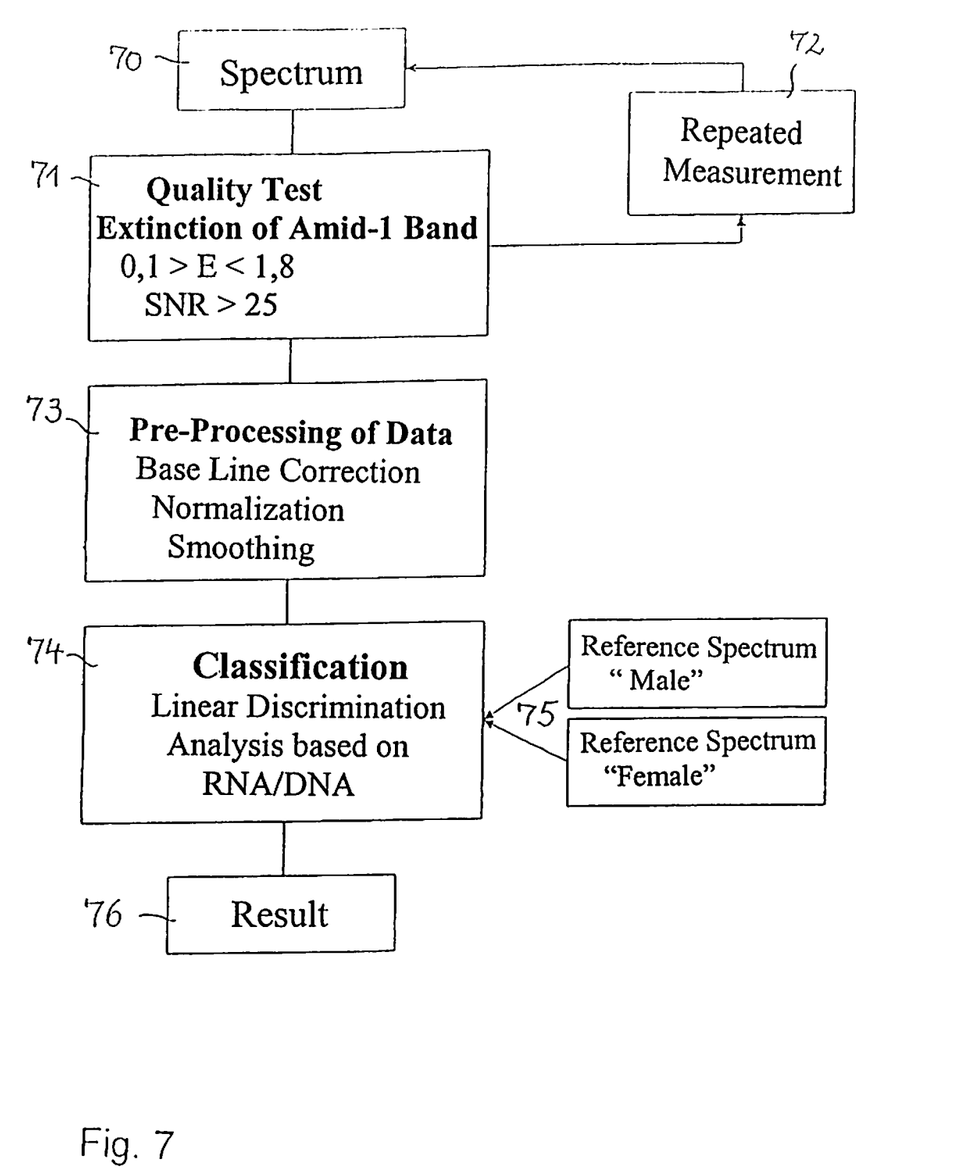

According to the invention an optical crystal is used as the probe 4, with the rapid and non-reactive receiving an infrared and/or near infrared spectrum 70, as shown in FIG. 7, optical outside when exploiting an attenuated total reflection 31 within the optical crystal 4 carried out by the existing evanescent field 21 at an output surface 27 evanescent field 21 in the region 29 of the germinal disc 3, wherein there occurs a different attenuation/extinction due to different spectral absorption of different gender germinal disc cells 23, wherein the positioning of the optical crystal 4 is accompanied by a permanent automatic analysis of the crystal-inside totally reflected spectra by the provision of gender-germ disc cells 23, until the sex of the fertilized egg 13 is unequivocally indicated.

The automatic positioning of the optical crystal 4 with the crystal tip/output surface 27 in relation to the germinal disc cells 3 is carried out until the evanescent field 21 of the total reflection 31 at the crystal tip/output surface 27 captures the germinal disc 3 and the optical crystal 4 has reached its final disc mapping position 28, at which position the evanescent field 21 interacts with the embryonic disc cells 23.

The disc mapping position 28 of the optical crystal 4 can be directed in all directions in space possible in order to hit as precisely as possible the germinal disc 3 and the embryonic disc cells 23 of the germinal disc 3.

During the positioning process of the optical crystal 4, the returned totally reflected IR and/or NIR spectra 70 are permanently recorded and fed to an evaluation, wherein an automatic classification of returned spectra 70 is performed using the spectral fingerprint in proteins, lipids and nucleic acids.

In the gender-absorption of the incident IR and/or NIR light, the embryonic disc cells 23 were identified by means of absorption bands of nucleic acids (DNA and RNA) in the detector 32 so that the gender of the tested bird egg 13 can be determined and displayed.

The spectroscopic analysis is performed in the evaluation unit 11 with the IR or NIR spectroscopy or using a Fourier-transform infrared spectroscopy, with the evaluation preferably including a mathematical classification algorithm.

The inclusion of the classification of the measured FTIR spectra 70 in the context of the analysis is shown in FIG. 7.

A six-step process is roughly indicated for the implementation of the spectral classification and its result output:
  First Step 71 of the quality testing of the measurement for detecting the spectra 70 and eliminating inadequate detected spectra, with which no evaluation can be carried out, considering to check compliance if the recorded spectra 70 meet the following requirements/criteria:
    The absorbance E of the amide I-band of 47 as the strongest absorption band, which is shown in FIG. 4a is proposed to be mainly between 0.1 and 1.8 with 0.1>E>1.8, wherein over 1.8 no linear relationship between concentration and absorbance can be guaranteed,
    The signal to noise ratio (SNR) of the amide-I band 47 has at least a value of 25:1.
  Second Step 72 of the repeated measurement, if the two criteria of step 71 are not achieved,
  Third Step 73 of the data pre-treatment with
    A reduction in the spectral region at a wave number range between 1000 and 1800 cm-1, wherein the wave length region comprises the so-called fingerprint, the absorptions of proteins, lipids, nucleic acids and containing other concerned compounds,
    A suppression of noise using Savitzky-Golayfilter,
    A correction of the baseline, of the linear function and the correction of the off-sets,
    A normalization of the spectra 70 integral extinction by area normalization.
  Fourth Step 74 of the spectral classification with
the use of a supported (English, supervised) classification. The LDA—linear discriminance analysis—can be used as a classification method. Other methods, such as non-linear procedure and/or methods or supporting facilities or SIMCA can be used. The LDA classifies several spectral ranges, i.e., the absorbance values of these areas. In this case, the classification is based primarily on the ratio of the phosphate vibrations of DNA and RNA. Due to the differences in the genome, male germ cells and female germ cells of embryonic disc cells can be distinguished.

Fifth Step 75 of the verification, which will require a set of reference spectra with reference spectra "male" and reference spectra "female" is required with known gender association. The algorithm compares the spectrum 70 with other spectra of the sex class and analyzes the similarity of the unknown spectrum 70 with the known spectra.

Sixth Step 76 to output the results of determining the respective gender of each bird egg 13, 130.

Figure 5:
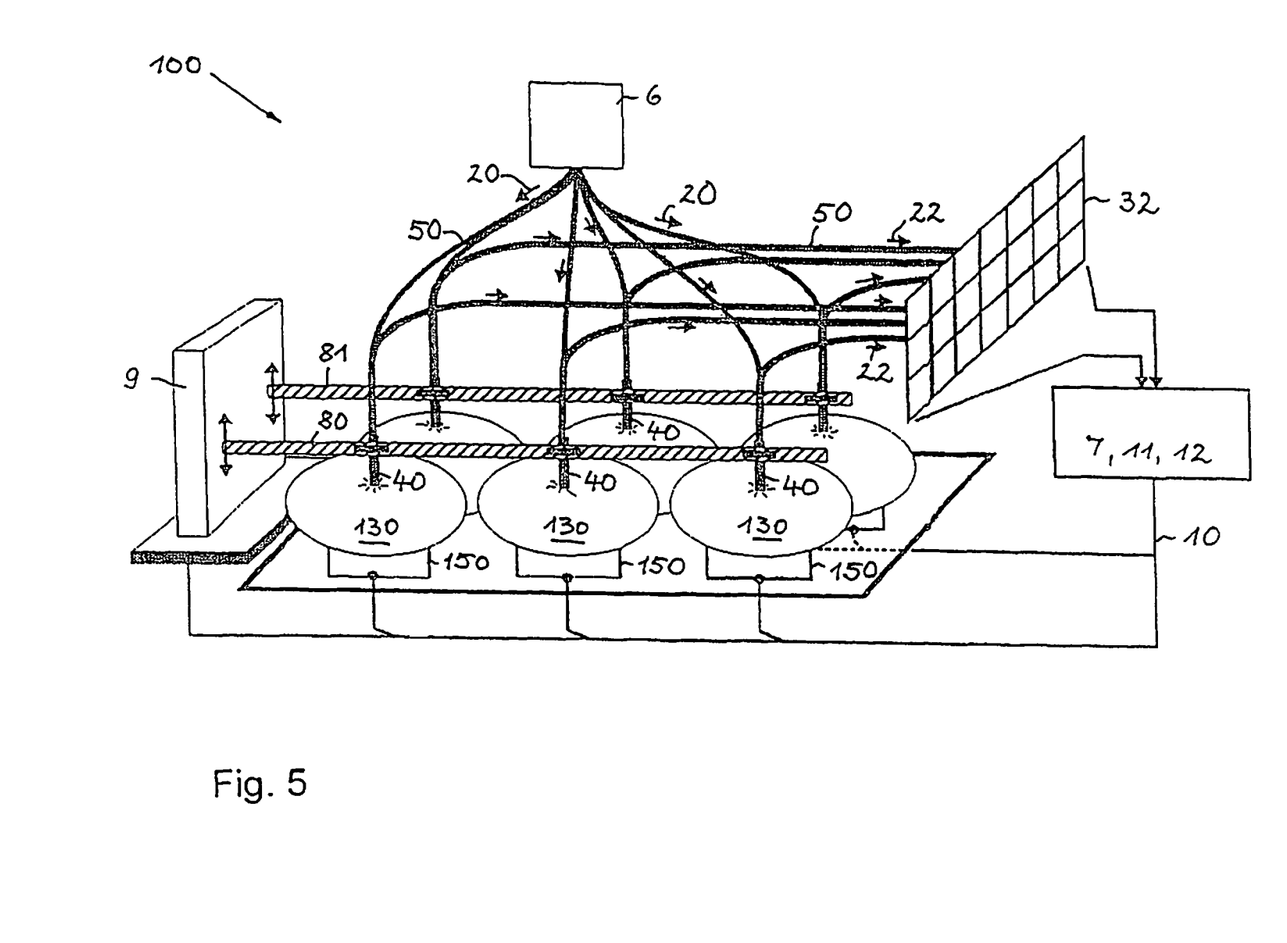
FIG. 5 shows a schematic representation of an apparatus for determining the sex of fertilized and not embryonated bird eggs by means of a parallel measurement of many bird eggs using optical fibers which are at the ends directed to the egg connected to optical crystals for beam guidance.

In FIG. 5 is a schematic illustration of a device 100 for determining the sex of many fertilized and not embryonated bird eggs 130 by means of a parallel measurement of the spectra 70 of many bird eggs 130 by use of optical fibers 50 which are connected to optical crystals 40, for beam guidance is shown.

The device 100 for determining the sex of fertilized and non-incubated bird eggs 130 contains
- At least one egg position support 150 for locking at least one bird egg 130
- A height adjustment device 9 with two holding arms 80, 81,
- More than one optical crystals 40 formed as a probe, which are fastened to the holding arms 80.81,
- A control unit 11, at least for the operation of egg arresting egg supports 150 and the height adjustment device 9,
- A spectral light source 6, which emits an IR and/or NIR light beam,
- a detector 32 for receiving the returned IR and/or NIR light,
- A plurality of optical elements 50 for associated guided optical paths 20 between the spectral light source 6 and the optical crystals 40 and for returned beam paths 22 between the optical crystals 40 and the detector 32 as well as
- An evaluation unit 7 and a display unit 12 connected to the detector 32, The egg position system 150 in connection with the control unit 11 can be formed into a device for automatic individual positioning of the respective egg 130

Figure 6:
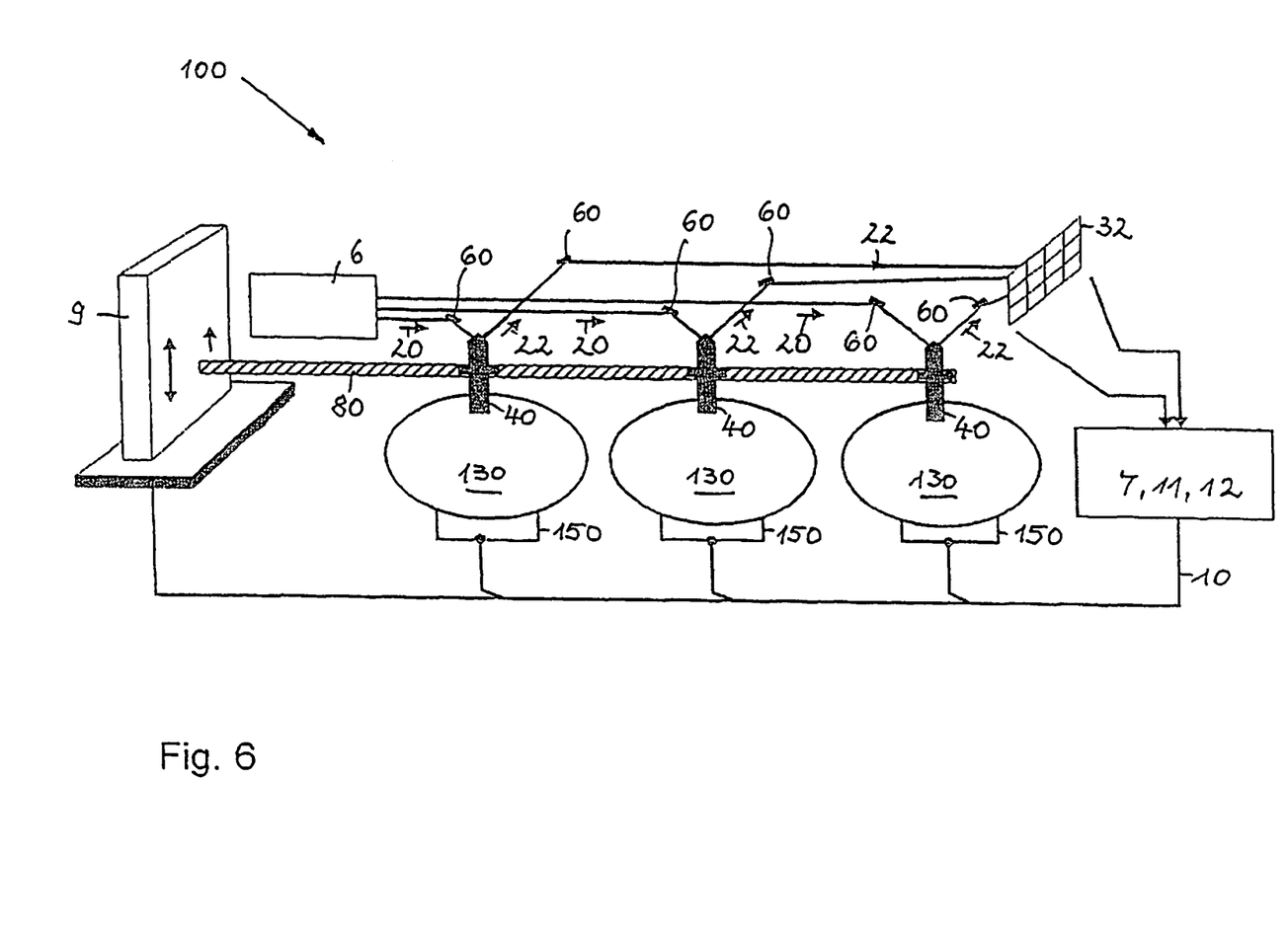
FIG. 6 is a schematic illustration of an apparatus for determining the sex of fertilized and non-incubated bird eggs using a parallel measurement of many birds' eggs according to FIG. 5 using mirrors/mirror systems for beam guiding light and imaginative angles specifically sanded crystal surfaces instead of the input optical fibers and FIG. 7 is a block diagram for explaining the operational mode for the classification of the recirculated and detected spectra.

FIG. 6 shows another specification and schematic representation of the device 100 to determine the sex of fertilized and non-incubated bird's eggs 130 by means of parallel measurements of the spectra 70 sharpened by many birds' eggs 130 according to FIG. 5 under use of mirrors 60 or mirror systems for beam control and incident angle-specific crystal input surfaces 34, as shown in FIG. 3, or crystalline cone input surfaces instead of the optical fibers 50.

Simultaneously with the devices 100, a plurality or array-equipped arranged many bird eggs can be measured 130, with either optical crystals are arranged in several array-like crystals 40 and each coupled to a separate optical fiber 50 or the totally reflected light without fibers 50, but with mirrors 60 is fed directly to an IR and/or NIR-sensitive array detector 32.

LIST OF REFERENCE NUMERALS 1 device for distinguishing gender of fertilized eggs
2 egg yolks
3 blastodisc, germial disc
4 Optical Crystal
5 Optical Element
6 light source for IR and/or NIR light
7 evaluation
8 suppert arm
9 height adjustment
10 Power supply and signal connection lines
11 control unit
12 display unit
13 No
14 eggshell
15 egg position edition
16 device for detecting the position of the germinal disc
17 Hole
18 gold layer
19 Metal Coating
20 guided beam
21 Evaneszentes Feld
22 Return-guided beam
23 blastoderm cell, sh
24 Dottermembran
25 supply and signal connection lines
26 Surface
27 Lower output surface, output area
28 Washer assignment position
29 area
30 Management of the embryonic disc
31 Total Reflection
32 detector
33 crystal point
34 crystal input surface
35 line
40 crystals
41 first arrow for wavenumber vi
42 second arrow for wave number v 3
43 third arrow for wave number v 4
44 fourth arrow for wave number v 2
45 normalized spectral absorbance male
46 normalized spectral absorbance female
Amid 47-I-Band
50 fibers
60 levels
70 spectra
Step 71 tests the quality of the measurement
Step 72 of the repeated measures
73 step of data pretreatment
74 Step to the spectral classification
75 step of verifying
76 step for outputting the results
80 Haftearm
81 arm
100 device
130 eggs
150 Eipositions-edition
v 1 wavenumber
V 2 wavenumber
V 3 wavenumber
v 4 wavenumber
E 2 normalized absorbance at wavenumber v 2
E 4 normalized absorbance at wavenumber v 4
E 2' normalized absorbance at wavenumber v 2
E 4' normalized absorbance at wavenumber v 4

The invention claimed is:

1. A method for determining the sex of fertilized and non-incubated bird's eggs, wherein a bird's egg comprises a solid egg shell, an egg yolk surrounded by the solid egg shell and other egg envelopes and a germinal disc coordinated to the egg yolk with the following steps: furnishing a hole in the egg shell; positioning the hole in a region of the germinal disc; guiding a probe including an optical crystal through the hole toward the germinal disc having germinal disc cells; measuring spectra through the hole in the egg shell with the probe including the optical crystal; determinating the germinal disc cells spectroscopically in-ovo; receiving rapidly and backreaction free infrared spectra or near infrared spectra at the optical crystal; using an attenuated total reflection within the optical crystal by an evanescent field in a region of the germinal disc; inducing attenuation or extinction due to a spectral absorption of gender specific germinal disc cells; accompanying the positioning of the optical crystal by a permanent automatic evaluation of the recirculated spectra for a determination of gender specific germinal disc cells; evaluating the spectra with an evaluation unit; identifying the sex of the fertilized egg through automatic classification of reflection spectra; displaying unequivocally the sex of the fertilized egg with a display unit.

2. The method according to claim 1, further comprising carrying out the positioning of the optical crystal automatically with a crystal tip or an output surface in relation to the germinal disc cells and until the evanescent field of a total reflection at the crystal tip or at the output surface captures the germinal disc and the optical crystal has reached its final disc mapping position; and interacting the evanescent field with the germinal disc cells in the final disc mapping position.

3. The method according to claim 1, further comprising directing a disc mapping position of the optical crystal in all directions in space possible in order to hit the germinal disc as precisely as possible.

4. The method according to claim 3, further comprising absorbing gender specifically the incident IR or NIR light; identifying the embryonic disc cells by means of absorption bands of nucleic acids (DNA and RNA) in a detector; and determining and displaying the gender of the tested bird egg.

5. The method according to claim 2, further comprising permanently recording returned totally reflected IR or NIR spectra during the positioning process of the optical crystal; feeding the returned totally reflected IR or NIR spectra to an evaluation; performing an automatic classification of returned spectra; using spectral fingerprint in proteins, lipids and nucleic acids.

6. The method according to claim 1, further comprising performing a spectroscopic analysis in the evaluation unit with IR or NIR spectroscopy or using a Fourier-transform infrared spectroscopy; evaluating the spectra with a mathematical classification algorithm.

7. The method according to claim 1, further comprising simultaneously measuring several eggs are measured simultaneously while at a distance from each other; arranging either several optical crystals like a field at a distance from each other; coupling the optical crystals in each case with a separate optical fiber; guiding and the light by way of mirrors or mirror systems for beam deflection from the spectral light source; guiding field-like after gender specific absorption on an IR- or NIR-sensitive detector with detector elements or pixels.

8. A device for determining the gender of fertilized and not hatched bird eggs, comprising an avian egg exhibiting a solid egg shell, an egg yolk, surrounded by the egg shell, fetal membranes and a germinal disc coordinated to the egg yolk; a microscopically small hole in the egg shell; a probe formed as an optical crystal for measuring a spectrum through the microscopically small hole of the egg shell is guided there through toward the germinal disc with germinal disc cells; an egg position support for locking of the avian egg; a height level adjusting device with a supporting arm, wherein the probe is fixed to the support arm; a control unit connected to the egg arresting egg position support and the height level adjusting device; a spectral light source which emits an IR or NIR light beam; an optical element for a guided beam path between the spectral light source and the optical crystal, as well as for a recirculated beam path between the optical crystal and a detector as well as an evaluation unit connected to the detector, and to a display unit, wherein the height adjustment device establishes the height of the holding arm and therewith of the optical crystal, and can be adjusted relative to a position of the germinal disc, and wherein the optical crystal can be positioned in the region of the germinal disc in a disc mapping position, wherein an evanescent field forms in an output area over the optical crystal, wherein the output area is directed to the germinal disc upon total reflection over the optical crystal, wherein the evanescent field overlaps the germinal disc, wherein the germinal disc cells interacting with the evanescent field perform a gender specific absorption of light out of the introduced beam path, wherein the light totally reflected is guided within the optical crystal and finally through the optical element to the detector for registration, wherein the registered spectral signals are transmitted from the detector for evaluation and display of the gender.

9. The device according to claim 8, wherein the hole in the egg shell is either already present prior to placement of the optical crystal in the disc mapping position or is entered by the optical crystal itself during a passage of the optical crystal through the egg shell.

10. The device according to claim 8, further comprising a device for detecting the position of the germinal disc in the avian egg is coordinated to the germinal disk.

11. The device according to claim 8, wherein the disc mapping position of the optical crystal can be adjusted in the region of the germinal disc with the device for detecting the position of the germinal disc within the egg through the support arm, which is formed height level adjustable and pivotable.

12. The device according to claim 8, wherein the device for detecting the position of the embryonic disc in the bird egg is connected to the control unit through at least one power supply and signal technology line.

13. The device according to claim 8, wherein the device for detecting the position of the germinal disc is connected to the height adjustment device and the egg position support.

14. The device according to claim 8, wherein the device for detecting the position of the germinal disc, the height adjustment device and the egg position pad are connected and fixed by way of program-technical means to a coordination in the control unit of the position of the germinal disc and the precision target mapping position of the optical crystal in the region of the germinal disc.

15. The device according to claim 8, wherein the optical element is a flexible optical fiber and wherein the optical crystal is connected to the flexible optical fiber, wherein the light beam from the spectral light source to the optical crystal as well as also from the optical crystal to the detector is conducted through the flexible optical fiber.

16. The device according to claim 8, wherein the optical crystal is formed cylindrically and is held with different formed crystal end faces or crystal ends, with a planar, round or oval output area or also however with an acute crystal tip.

17. The device according to claim 16, wherein the optical crystal is formed like a needle in the region of the lower output area.

18. The device according to claim 16, wherein
the optical crystal consists of glass or sapphire for measurements with IR-light.

19. The device according to claim 16, wherein
the optical crystal consists of a composite, wherein the crystal tip in the region of the output area consists of diamond in view of the needle shape of the crystal.

20. The device according to claim 8, wherein the optical crystal is formed cylindrically and is held in a cylindrical metal jacket, wherein the cylindrical metal jacket (19) stands in connection with the holding arm.

21. The device according to claim 20, wherein a gold layer is applied between the metal jacket and the surface of the optical crystal for improving the reflecting properties.

22. The device according to claim 8, wherein the optical crystal consists of an IR-transparent and at the same time hard material out of germanium, silicon, calcium fluoride ($CaF_2$), barium fluoride ($BaF_2$), zink selenide (ZnSe), or zink sulphide (ZnS).

23. The device according to claim 8, further comprising a pixelized detector as IR- or NIR-sensitive detector employed in order to pixel coordinated capture simultaneously and parallel back guided spectra of many eggs to be tested from the coordinated optical crystals.

* * * * *